United States Patent
Moskovich et al.

(10) Patent No.: US 8,813,296 B2
(45) Date of Patent: *Aug. 26, 2014

(54) ORAL CARE IMPLEMENT HAVING MULTI-COMPONENT HANDLE

(71) Applicant: Colgate-Palmolive Company, New York, NY (US)

(72) Inventors: Robert Moskovich, East Brunswick, NJ (US); Marco Bohner, Sempach (CH); Michael Rooney, Millburn, NJ (US); Eduardo Jimenez, Manalapan, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/023,077

(22) Filed: Sep. 10, 2013

(65) Prior Publication Data

US 2014/0041140 A1    Feb. 13, 2014

Related U.S. Application Data

(63) Continuation of application No. 12/641,698, filed on Dec. 18, 2009, now Pat. No. 8,549,691.

(51) Int. Cl.
 *A46B 5/02*      (2006.01)
(52) U.S. Cl.
 USPC ...... 15/143.1; 15/167.1; 16/430; 16/DIG. 18; 16/DIG. 19
(58) Field of Classification Search
 USPC ............... 15/143.1, 167.1; 16/431, 436, 430, 16/DIG. 12, DIG. 18, DIG. 19
 See application file for complete search history.

(56) References Cited

U.S. PATENT DOCUMENTS

| | | |
|---|---|---|
| 4,283,808 A | 8/1981 | Beebe |
| 5,339,482 A | 8/1994 | Desimone et al. |
| 5,398,369 A | 3/1995 | Heinzelman et al. |
| 5,761,759 A | 6/1998 | Leversby et al. |
| 5,781,958 A | 7/1998 | Meessmann et al. |
| 6,051,176 A | 4/2000 | Boucherie |
| 6,108,849 A | 8/2000 | Weihrauch |
| 6,108,869 A | 8/2000 | Meessmann et al. |
| 6,158,444 A | 12/2000 | Weihrauch |
| 6,234,798 B1 | 5/2001 | Beals et al. |
| 6,276,019 B1 | 8/2001 | Leversby et al. |
| 6,276,020 B1 | 8/2001 | Leversby et al. |
| 6,298,516 B1 | 10/2001 | Beals et al. |
| 6,357,074 B1 | 3/2002 | Weihrauch |
| 6,397,425 B1 | 6/2002 | Szczech et al. |
| 6,601,272 B2 | 8/2003 | Stvartak et al. |
| 6,687,940 B1 | 2/2004 | Gross et al. |

(Continued)

FOREIGN PATENT DOCUMENTS

| | | |
|---|---|---|
| EP | 1397976 | 3/2004 |
| EP | 1621106 | 2/2006 |
| JP | 7-327737 | 12/1995 |
| JP | 11-75938 | 3/1999 |

(Continued)

*Primary Examiner* — Mark Spisich
(74) *Attorney, Agent, or Firm* — Thibault Fayette

(57) ABSTRACT

An oral care implement having a multi-component handle, and method of manufacturing the same. The invention can be a method of forming a handle for an oral care implement comprising: a) forming a core structure of a first hard plastic; b) forming an elongated handle body of a second hard plastic that at least partially surrounds the core structure so that opposing lateral surfaces of the core structure remain exposed; and c) forming a grip cover of a resilient material over at least a portion of the elongated handle body.

20 Claims, 10 Drawing Sheets

(56) References Cited

U.S. PATENT DOCUMENTS

| | | |
|---|---|---|
| 6,783,346 B2 | 8/2004 | Bodmer et al. |
| 6,854,965 B2 | 2/2005 | Ebner et al. |
| 7,264,868 B2 | 9/2007 | Ajbani et al. |
| 7,415,788 B2 | 8/2008 | Little et al. |
| 2003/0070259 A1 | 4/2003 | Brown et al. |
| 2004/0010876 A1 | 1/2004 | Kraemer |
| 2005/0015907 A1 | 1/2005 | Georgi et al. |
| 2006/0230652 A1 | 10/2006 | Little |
| 2008/0315668 A1 | 12/2008 | Huber et al. |
| 2009/0183331 A1 | 7/2009 | Gross et al. |
| 2009/0188063 A1 | 7/2009 | Baertschi et al. |
| 2009/0193600 A1 | 8/2009 | Pennell et al. |

FOREIGN PATENT DOCUMENTS

| | | |
|---|---|---|
| JP | 11-318952 | 11/1999 |
| JP | 2000-41737 | 2/2000 |
| JP | 2001-178538 | 7/2001 |
| JP | 2001-299450 | 10/2001 |
| JP | 2002-18895 | 1/2002 |
| JP | 2002-153322 | 5/2002 |
| JP | 2002-336049 | 11/2002 |
| JP | 2003-189936 | 7/2003 |
| JP | 2003-265232 | 9/2003 |
| JP | 2007-190439 | 8/2008 |
| WO | WO2004026162 | 4/2004 |
| WO | 2006005216 | 1/2006 |
| WO | WO2007073917 | 7/2007 |
| WO | WO2008000800 | 1/2008 |
| WO | WO2008064873 | 6/2008 |

ORAL CARE IMPLEMENT HAVING MULTI-COMPONENT HANDLE

CROSS-REFERENCE TO RELATED PATENT APPLICATIONS

The present application is a continuation of U.S. patent application Ser. No. 12/641,698, filed Dec. 18, 2009 now U.S. Pat. No. 8,549,691, the entirety of which is hereby incorporated by reference in its entirety.

FIELD OF THE INVENTION

The present invention relates generally to oral care implements, and specifically to oral care implements, such as toothbrushes, having a handle constructed of multiple components and/or materials.

BACKGROUND OF THE INVENTION

Oral care implements, such as toothbrushes, are mass-produced articles and must therefore allow cost-effective production. Toothbrushes made of a single plastic material and toothbrushes made of two plastic components, which are produced for example by a two component injection molding process, are known. In the latter case, known toothbrushes generally comprise two parts: a first part made of a hard plastic material, for example polypropylene; and a second part made of a resilient plastic material, for example a thermoplastic elastomer. Typically, the first part, which is made of the hard plastic material, forms the structural portion of the handle and has a recess or channel formed therein. This recess is filled with the resilient plastic material, thereby forming the second part which acts as a gripping surface or cover.

The hard plastic and the resilient soft plastic are selected so that they bond with one another at the surface where the two plastic parts touch. In comparison with a toothbrush made of only one plastic material, this provides greater scope for design. Since, however, the two plastic materials have to bond with one another during the injection-molding operation, there are restrictions in the selection of the plastic materials and consequently in the design of the toothbrush.

One solution to the limitation that two plastic materials must bond with one another during the injection molding operation has been introduced by which a handle can be formed by two plastics that do not chemically bond within one another during the injection molding operation but rather utilize a mechanical connection, such as by inter-fitting portions of the two plastic components or by shrinking one plastic component about the other. With respect to creating a two component toothbrush having a grip cover over a hard plastic body, this known method is limited in its design capability to a tubular sleeve that receives a cylindrical core structure within its cavity so as to circumferentially surround the entire circumference of the cylindrical core structure. This arrangement is limiting in both possible designs for the handle and the fact that the resulting handle must either be bulky or sacrifice strength.

Another oral care implement having a multi-component handle that is known in the art includes a gripping region having a thermoplastic elastomer ("TPE") grip surface with a plurality of spaced slot openings exposing portions of a hard plastic base. This handle also includes an inclined portion and a soft TPE grip body extending through the hard plastic base of the handle to form opposite finger grips on the inclined portion of the handle. This soft grip body provides shifting of a mass centroid during use. In this construction, the handle of the oral care implement comprises three components, a hard plastic handle body, a grip cover/surface formed of a first TPE, and a grip body formed of a second TPE which is softer than the first TPE.

A need exists for an oral care implement, and method of manufacturing the same, that has a handle having greater design flexibility, is more cost-effective to mass produce, and/or affords comfort and control to the user during use.

SUMMARY OF THE INVENTION

In one aspect, the invention is directed to an oral care implement having a multi-component handle constructed of at least four components constructed of different materials. In another aspect, the invention is directed to an oral care implement having a multi-component handle having a core structure, an elongated handle structure at least partially surrounding the core structure, and a grip cover strategically located on the elongated handle body to conceal through holes in the elongated body resulting from supporting the core structure during the injection molding process.

In one embodiment, the invention may be an oral care implement comprising: a handle having a proximal end and a distal end; a head connected to the distal end of the handle; the handle comprising a first component constructed of a first material, a second component constructed of a second material, a third component constructed of a third material and a fourth component constructed of a fourth material.

In another embodiment, the invention may be an oral care implement comprising: a head; a handle having a distal end and a proximal end, the head connected to the distal end of the handle; the handle comprising a core structure constructed of a first rigid material and an elongated handle body constructed of a second rigid material, the core structure disposed within a through slot of the elongated handle body so that the core structure is exposed on opposite lateral surfaces of the handle; and a grip cover constructed of a resilient material, the grip cover covering a front surface, a rear surface and a proximal end surface of the elongated handle body.

In a further embodiment, the invention may be an oral care implement comprising: a head; a handle having a distal end and a proximal end, the head connected to the distal end of the handle; the handle comprising a core structure constructed of a first rigid material and an elongated handle body constructed of a second rigid material that does not form a chemical bond with the first material during an injection molding process; the core structure disposed within a through slot of the elongated handle body so that the core structure is exposed on opposite surfaces of the handle; at least one through hole on a first surface of the elongated handle body through which the core structure is exposed and at least one through hole on a second surface of the elongated handle body through which the core structure is exposed, the second surface opposite the first surface; the core structure comprising a first protuberance that extends into the through hole on the first surface of the elongated handle body and a second protuberance that extends into the through hole on the second surface of the elongated handle body; and a grip cover constructed of a resilient material covering the through hole on the first surface of the elongated handle body and the through hole on the second surface of the elongated handle body, the resilient material forming a chemical bond with the second material during an injection molding process.

In a yet further embodiment, the invention may be a method of forming a handle for an oral care implement comprising: a) injecting a liquefied first plastic into a first mold cavity to form a core structure of the first plastic; b) supporting the core structure within a second mold cavity with a gripping member that contacts the core structure at two or more points of contact on opposite surfaces of the core structure; c) injecting a liquefied second plastic into the second mold cavity to form an elongated handle body that at least partially surrounds the core structure, thereby forming a handle assembly, the elongated handle body surrounding the gripping member resulting in a through hole in the elongated handle body for each point of contact, the points of contact exposed via the through holes; d) supporting the handle assembly in a third mold cavity; and e) injecting a liquefied resilient material into the third mold cavity to form a grip cover over the elongated handle body, the grip cover overlying the through holes.

In still a further embodiment, the invention may be an oral care implement comprising: a head; a handle having a distal end and a proximal end, the head connected to the distal end of the handle; the handle comprising a core structure constructed of a transparent rigid material and an elongated handle body constructed of an opaque rigid material; the core structure disposed within a through slot of the elongated handle body so that the core structure is exposed on opposite surfaces of the handle so as to form a window through the handle; and a plurality of facets formed into an interior of the core structure that are visible through the window and reflect visible light.

In an even further embodiment, the invention can be a method of forming a handle for an oral care implement comprising: a) forming a core structure of a first hard plastic; b) forming an elongated handle body of a second hard plastic that at least partially surrounds the core structure so that opposing lateral surfaces of the core structure remain exposed; and c) forming a grip cover of a resilient material over at least a portion of the elongated handle body.

In another embodiment, the invention can be an oral care implement comprising: a handle having a proximal end and a distal end; a head connected to the distal end of the handle; the handle comprising a core structure comprising a first rigid material, an elongated handle body comprising a second rigid material, a grip cover comprising a resilient material; wherein the elongated handle body comprises the head; and wherein the core structure is disposed in a through slot that extends from opposite surfaces of the elongated handle body, and wherein surfaces of the core structure remain exposed via the through slot.

BRIEF DESCRIPTION OF THE DRAWINGS

This invention is capable of use in a broad array of oral care implements and hygiene products. The drawings illustrate one use of the invention and are not to be construed as the only embodiment of the invention.

DETAILED DESCRIPTION OF THE INVENTION

Figure 1:
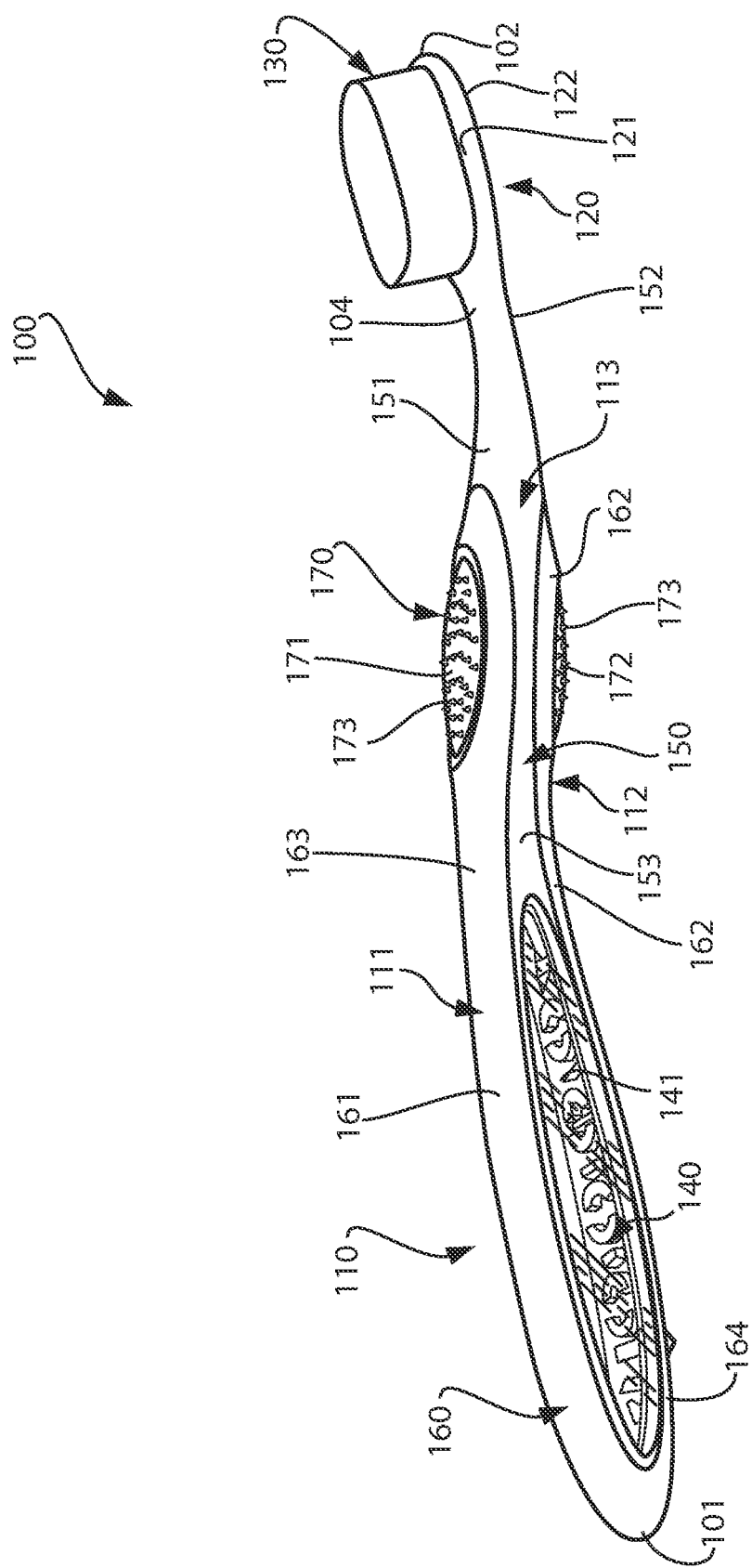
FIG. 1 is a perspective view of an toothbrush according to one embodiment of the present invention.

In the following description, the invention is discussed in terms of a manual toothbrush, and method of manufacturing the same, having the inventive multi-component handle. However, in other forms, the invention could be in the form of other oral care implements including a soft-tissue cleansing implement, an inter-proximal pick, a flossing tool, a plaque scraper, a powered toothbrush, or other ansate implement designed for oral care. It is also to be understood that other embodiments may be utilized, and that structural and functional modifications may be made without departing from the scope of the present invention.

Referring first to FIGS. 1-4 concurrently, a toothbrush 100 is illustrated according to one embodiment of the present invention. The toothbrush 100 generally comprises a handle 110 and a head 120. The handle 110 provides the user with a mechanism by which he/she can readily grip and manipulate the toothbrush 100. The handle 110 includes ergonomic features which provide a high degree of control for the user while maintaining comfort. The head 120 is connected to a distal end 102 of the handle 110 and includes a set of teeth cleaning elements 130, which are generically illustrated.

Figure 2:
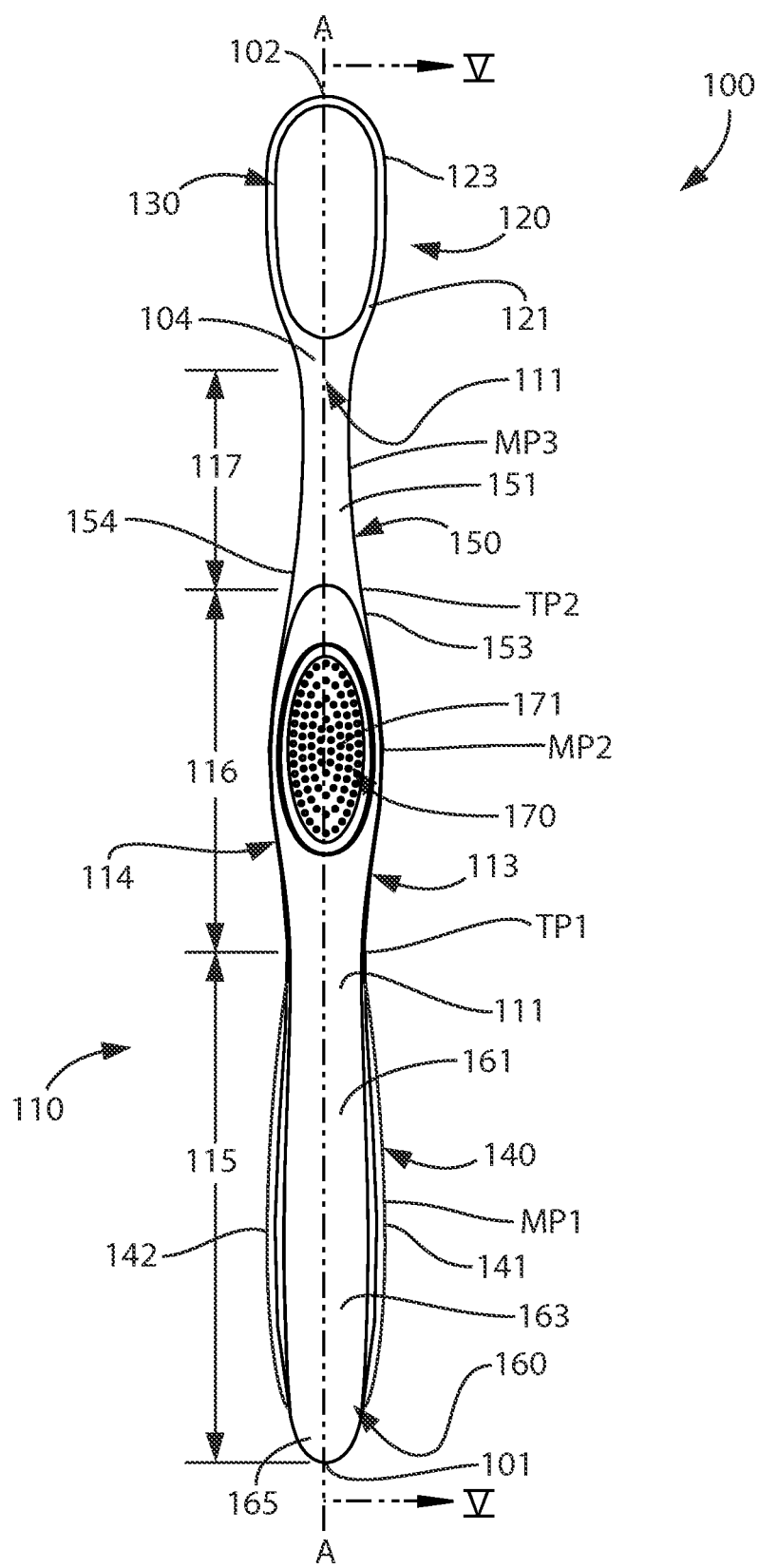
FIG. 2 is a front view of the toothbrush of FIG. 1 according to one embodiment of the present invention.
Figure 4:
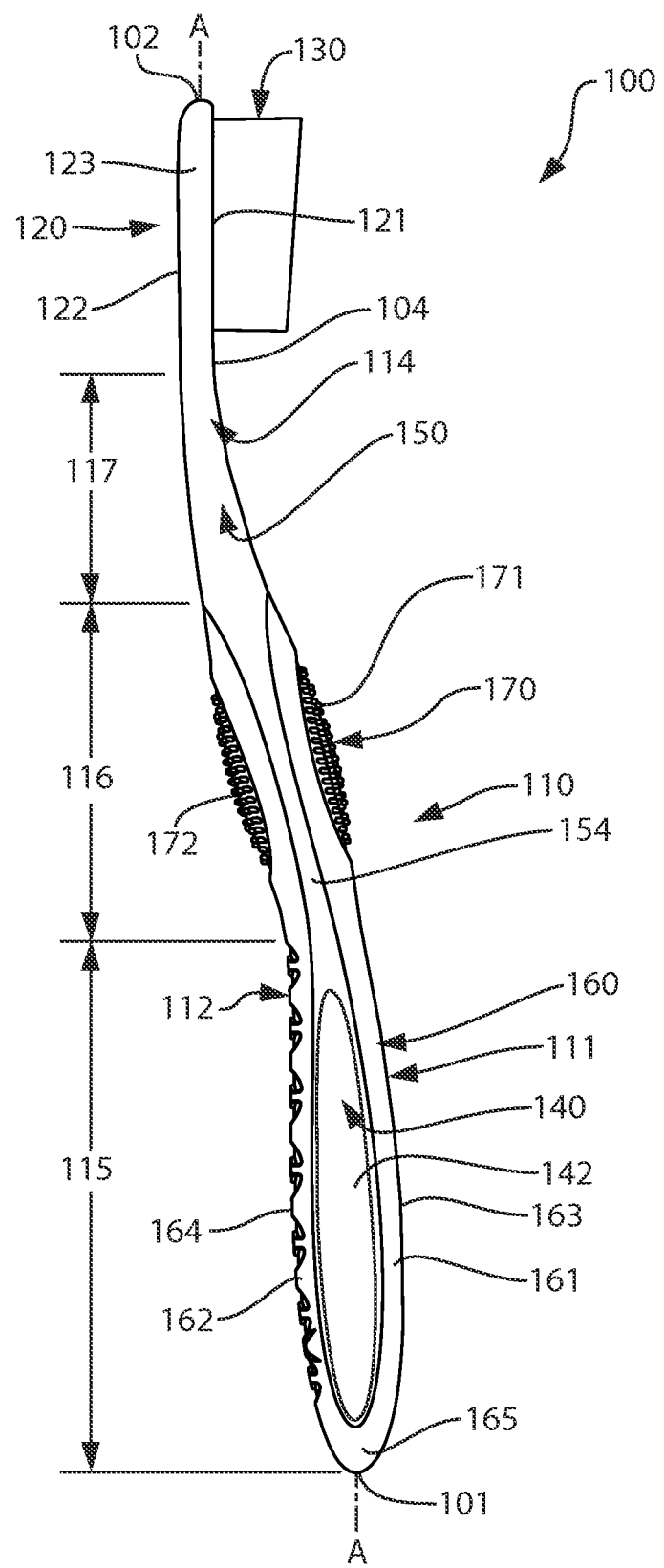
FIG. 4 is a left side lateral view of the toothbrush of FIG. 1 according to one embodiment of the present invention, the right side lateral view of which is a mirror image.

Generally, the toothbrush 100 extends from a proximal end 101 (which is also the proximal end of the handle 110) to a distal end 102 along a longitudinal axis A-A (illustrated in FIG. 2). Conceptually, the longitudinal axis A-A is a reference line that is generally coextensive with the three-dimensional center line of the handle 110 and the head 120. Because the handle 110 is a non-linear structure (as can be seen in FIG. 4 as viewed laterally) in the illustrated embodiment, the longitudinal axis A-A for toothbrush 100 is also non-linear in the illustrated embodiment. However, the invention is not so limited, and in certain embodiments, the toothbrush may have a simple linear arrangement and thus a substantially linear longitudinal axis A-A.

The head 120 is operably connected to the handle 110. As discussed in greater detail below, the head 110 and the handle 120 of the toothbrush 100 are preferably formed as an integral structure using an injection molding process. More specifically, in the exemplified embodiment, the head 120 is integrally formed with the elongated handle body 150 (discussed in greater detail below). However, in other embodiments, the handle 110 and the head 120 may be formed as separate components which are operably connected at a later stage of the manufacturing process by any suitable technique known in the art, including without limitation thermal welding, sonic welding, a tight-fit assembly, a coupling sleeve, adhesion, or fasteners. Whether the head 120 and the handle 110 are constructed as an integral piece or a multi-piece assembly (including connection techniques) is not limiting of the present invention in all embodiments. Furthermore, other manufacturing techniques may be used in place of and/or in addition to injection molding to create the handle 110 and/or the head 120 (or components thereof), such as milling and/or machining.

It should be noted that relative terms such as distal, middle, proximal, upper, lower, top, bottom, lateral, front, rear, left, right etc. are merely used to delineate relative positions of the components of the toothbrush 100 with respect to one another and are not intended to be in any further way limiting of the present invention.

The head 120 generally comprises a front surface 121 and a rear surface 122. The front surface 121 and the rear surface 122 of the head 120 can take on a wide variety of shapes and contours, none of which are limiting of the present invention. For example, the front and rear surfaces 121, 122 can be planar, contoured or combinations thereof. The front surface 121 and rear surface 122 are bound by a peripheral or lateral surface 123.

The set of teeth cleaning elements 130, which are generically illustrated as a block, are provided on and extend outward from the front surface 121 of the head 120 for cleaning contact with an oral surface, preferably teeth. While the set of cleaning elements 130 is particularly suited for brushing teeth, the set of cleaning elements 130 can also be used to clean oral soft tissue, such as a tongue, gums, or cheeks instead of or in addition to teeth. As used herein, the term "cleaning element" is used in a generic sense to refer to any structure that can be used to clean or massage an oral surface through relative surface contact.

Common examples of "cleaning elements" include, without limitation, filament bristles, fiber bristles, nylon bristles, spiral bristles, rubber bristles, elastomeric protrusions, flexible polymer protrusions, co-extruded filaments, flag bristles, crimped bristles, anti-bacterial bristles and combinations thereof and/or structures containing such materials or combinations.

The set of cleaning elements 130 can be connected to the head 120 in any manner known in the art. For example, anchor free tufting (AFT) could be used to mount the cleaning elements. In AFT, a plate or membrane is secured to the brush head such as by ultrasonic welding. The bristles (or other elastomeric elements) extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block. Staple technology may also be used.

Furthermore, if desired, the rear surface 122 may also comprise additional structures for oral cleaning, such as a soft tissue cleanser. Such soft tissue cleansers are typically constructed of a TPE and include one or more projections, such as nubs and/or ridges, for engaging and massaging soft oral tissue, such as the tongue.

The handle 110 of the toothbrush 100 generally comprises a front surface 111 and a rear surface 112 which is opposite the front surface 111. The handle 110 also comprises a right lateral surface 113 and a left lateral surface 114 opposite the right lateral surface 113. As best visible in FIG. 6, the front surface 111, the rear surface 112, the right lateral surface 113 and the left lateral surface 114 collectively form the outer surface of the handle 110, which has a generally elliptical lateral cross-sectional shape along its longitudinal length.

As will be described in greater detail below, the overall front surface 111 of the handle 110 is formed by the collective of the outer surface 163 of the front leg 161 of the grip cover 160, the front surface 171 of the grip body 170, and a portion of the front surface 151 of the elongated handle body 150. Similarly, the overall rear surface 112 of the handle 110 is formed by the collective of the outer surface 164 of the rear leg 162 of the grip cover 160, the rear surface 172 of the grip body 170, and a portion of the rear surface 152 of the elongated handle body 150. The overall right lateral surface 113 of the handle 110 is formed by the collective of the right lateral surface 153 of the elongated handle body 150 and the right lateral surface 141 of the core structure 140. Similarly, the overall left lateral surface 114 of the handle 110 is formed by the collective of the left lateral surface 154 of the elongated handle body 150 and the left lateral surface 142 of the core structure 140.

Figure 3:
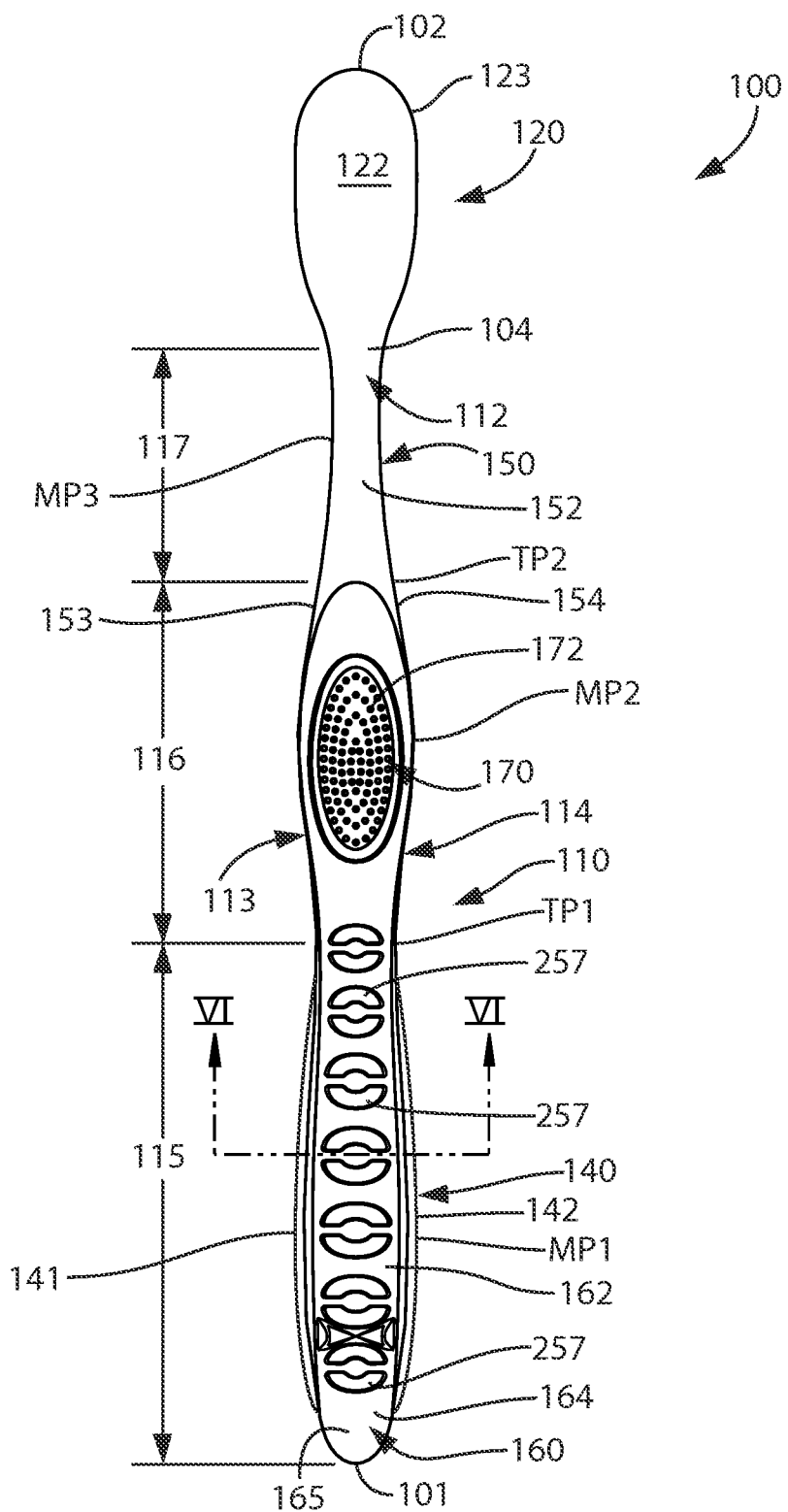
FIG. 3 is a rear view of the toothbrush of FIG. 1 according to one embodiment of the present invention.

As best shown in FIGS. 2-4, the handle 110 can be conceptually delineated in longitudinal sections comprising a proximal section 115, a middle section 116 and a neck section 117. The proximal section 115 is the portion or segment of the handle 110 that generally fits comfortably within the palm of the user. The middle section 116 forms the portion or segment of the handle 110 that generally fits comfortably between the user's thumb and index finger. The neck portion forms the portion or segment of the handle 110 that connects to the head 120.

The proximal section 115 longitudinally extends from the proximal end 101 of the toothbrush 100 to the middle section 116. The middle section 116 longitudinally extends from the proximal section 115 to the neck section 117. The neck section 117 extends from the middle section 116 to the head 120. While the head 120 is illustrated as being widened relative to the neck section 117 of the handle 110, the head 120 could in some constructions simply be a continuous extension or narrowing of the neck section 117 of the handle 110. The proximal section 115 comprises a transverse cross-sectional area that gradually increases from the proximal end 101 of the toothbrush 100 to a middle point MP1 of the proximal section 115. The transverse cross-sectional area of the proximal section 115 then gradually decreases from the middle point MP1 to the transition point TP1 between the proximal section 115 and the middle section 116. The middle section 116 has a transverse cross-sectional area that gradually increases from the transition point TP1 to the middle point MP2 of the middle section 116 and then gradually decreases from the middle point MP2 to the transition point TP2 between the middle section 116 and the neck section 117. The transverse cross-sectional area of the neck section 117 gradually decreases from the transition point TP2 to the middle point MP3 of the neck section and then increases from the middle point MP3 to the head 120. The handle 110 of the toothbrush 100 preferably has a maximum transverse cross-sectional area at middle point MP1 of the proximal section 115. The increasing and decreasing transverse cross-sectional area discussed above results in a handle 110 having an undulating structure which is more reliably and comfortably held within the user's hand. Further, this wide construction of the proximal and middle sections 115, 116 requires less fine motor control by the user and is, hence, easier to hold and manipulate.

Referring solely to FIG. 4, the middle section 116 is angled with respect to the proximal section 115 and the neck section 117. Thought of another way, the middle section 116 is inclined relative to the proximal section and the neck section to define an inclined portion or segment of the handle 110 that is positioned for comfortable gripping and to facilitate a desired offset positioning of the head relative to the proximal section 115. The angle of the incline is preferably 23 degrees, but may range between 5 to 40 degrees. The inclined nature of the middle section 116 relative to the proximal and neck sections 115, 117 allows for improved control of the handle 110 during brushing in which the head 120 can be more desirably positioned within the mouth to engage the tooth cleaning elements 130 against the teeth.

The core structure 140 is located within the proximal section 115 of the handle 110. The grip body 170 is located within the middle section 116 of the handle 110. The grip cover 160 covers both the proximal section 115 and the middle section 116 of the handle 110.

Figure 7:
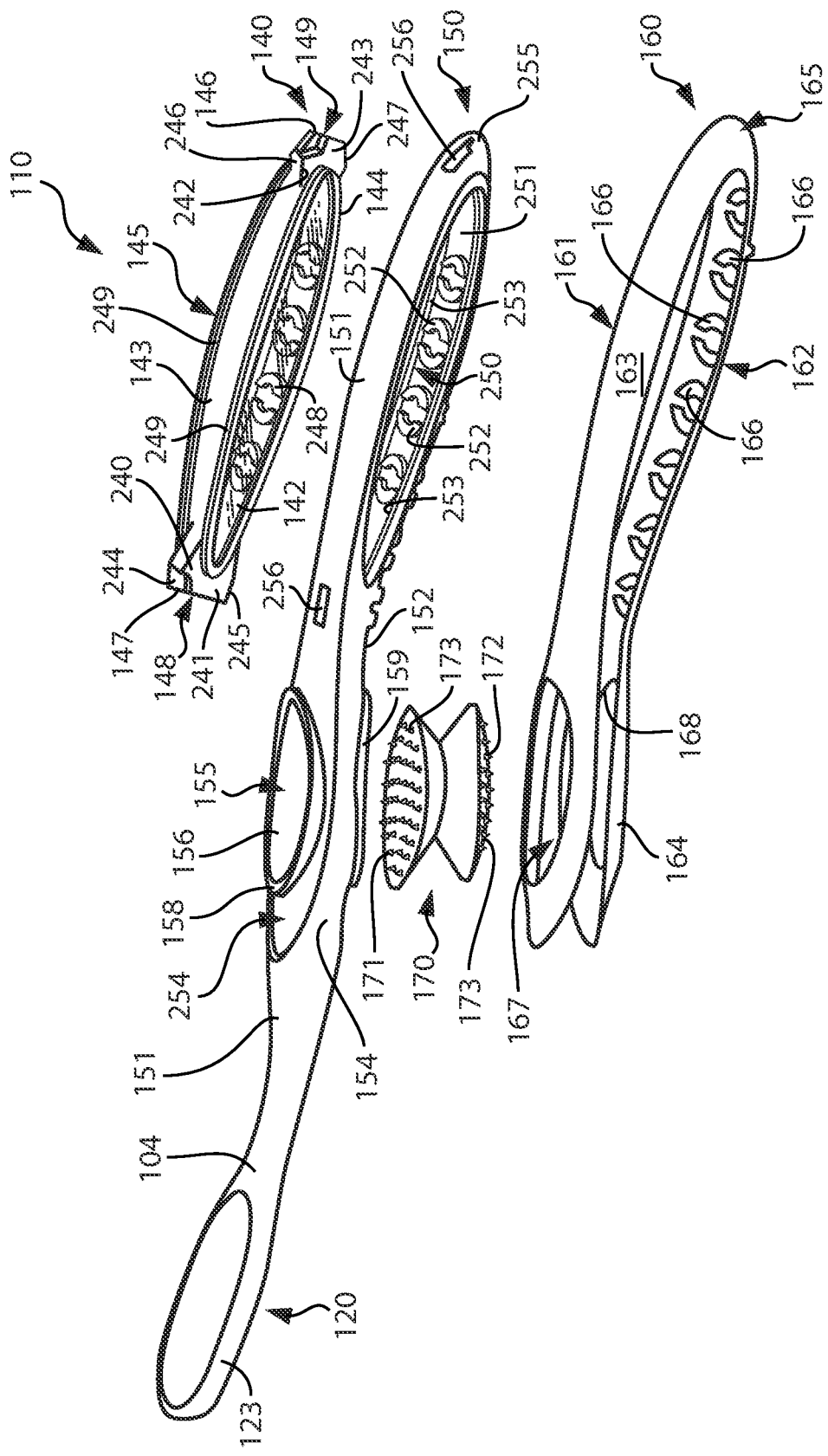
FIG. 7 is a perspective view of the toothbrush of FIG. 1 showing the four components of the handle in an exploded state according to one embodiment of the present invention.

Referring now to FIG. 7, the handle 110 is illustrated in an exploded state so that its four components are visible. The four components of the handle 110 include a core structure 140, an elongated handle body 150, a U-shaped grip cover 160 and a grip body 170. These components cooperatively form an ergonomic and cost effective handle 110 by which the user holds and manipulates the toothbrush. The structure of each of these components will now be described in detail.

The core structure 140 is an elongated structure extending from a proximal end 146 to a distal end 147. The core structure has a generally ovoid shaped solid body 145. The solid body 145 comprises a right lateral surface 141, a left lateral surface 142, a front surface 143 and a rear surface 144. The rear surface 144 is opposite the front surface 143 while the right lateral surface 141 is opposite the left lateral surface 142. All of the surfaces 141-144 are preferably convex surfaces, thereby giving the core structure 140 an elliptical transverse cross-sectional area that tapers toward both the proximal and distal ends 146, 147. Of course, the core structure can take on other shapes and sizes. Collectively, the surfaces 141-144 form the outer surface of the core structure 140.

A first protuberant structure 148 is located at the distal end 147 of the solid body 145. A second protuberant structure 149 is located at the proximal end 146 of the solid body 145. The first protuberant structure 148 comprises a first upper protuberance 240 protruding outward from the front surface 143 of the solid body 145 and a first lower protuberance 241 protruding outward from the rear surface 144 of the solid body 145. The second protuberance structure 149 comprises a second upper protuberance 242 protruding outward from the front surface 143 of the solid body 145 and a second lower protuberance 243 protruding outward from the rear surface 144 of the solid body 145. While two pairs of protuberances 240-241 and 242-243 are exemplified, the core structure 140 may of course have more or less protuberances as desired. Moreover, such protuberances may be located in different positions on the body 145 either longitudinally or laterally, or be omitted all together.

The first upper protuberance 240 comprises a contact surface 244. The second upper protuberance 243 comprises a contact surface 246. The first lower protuberance 241 comprises a contact surface 245. The second lower protuberance 243 comprises a contact surface 247. While it is desirable that the contact surfaces 244-247 be located on the protuberant structures 148, 149, the invention is not so limited and the contact surfaces 244-247 may be located directly on the body 145 in alternative embodiments. As will be described in greater detail below, the contact surfaces 244-247 provide points of contact that are used to support the core structure 140 during subsequent steps of the manufacturing process. Furthermore, and as will also be discussed in greater detail below, the protuberant structures 148, 149 mechanically engage the elongated handle body 150 to provide structural integrity to the handle 110 by prohibiting unwanted relative movement between the core structure 140 and the elongated handle body 150.

The rear surface 144 of the core structure comprises a plurality of arcuate grooves 248 that form depressions in the rear surface 144 of the core structure 140. The grooves 248 are preferably arcuate in shape and extend laterally across the substantial entirety of the width of the rear surface 144 in a spaced-apart manner. The arcuate grooves 248 are arranged in pairs wherein the two arcuate grooves 248 in each pair are oriented so that their concave sides oppose one another, thereby collectively forming a segmented circular groove.

Of course, other types of grooves and or ridges can be provided on the outer surface of the core structure 140 if desired. For example, a pair of spaced apart longitudinally extending linear grooves 249 could be provided on both the front and rear surfaces 143, 144 of the core structure 140 between which the arcuate grooves 248 are located.

The core structure 140 is preferably a unitary single component constructed of a rigid material, such as for example a hard plastic. Suitable hard plastics include polyethylene, polypropylene (PP), polyamide, polyester, cellulosics, SAN, acrylic, ABS or any other of the commonly known thermoplastics used in toothbrush manufacture. Preferably, the core structure 140 is constructed of a transparent rigid material. Suitable transparent rigid materials include without limitation clarified PP and clear polyesters, such as polyethylene terephthalate or a copolyester, such as poly-cyclohexylene dimethylene terephthalate, acid modified, polyester (PCTA) or styrene acrylonitrile (SAN), acrylonitrile butadiene styrene (ABS), polymethyl methacrylate (PMMA) or a cellulosic plastic, such as cellulose acetate propionate (CAP). Most preferably, the core structure is constructed of a substantially transparent SAN due to the benefits relating to cost, clarity and hardness characteristics.

When the core structure 140 is constructed of a transparent hard plastic, such as SAN, the grooves 248 formed into the rear surface 144 of the body 145 are visible through both the right and left lateral surfaces 141, 142 of the core structure 140 (which remain exposed when the toothbrush 100 is in an assembled state). As a result, the topography of the grooves 248 (formed by the floors and upstanding sidewalls of the grooves 248) act as facets that create the visible appearance of a shimmer or sparkle by deflecting and/or reflecting visible light, similar to the effect created by the facets of a diamond. Of course, in some embodiments of the invention, this shimmer or sparkle effect can be achieved by forming facets within the solid body 145 itself or in one or both of the front and rear surfaces 143, 144.

The elongated handle body 150 is preferably a unitary structure that integrally comprises the head 120 and provides the general structure and shape for the handle 110 of the toothbrush 100. The elongated handle body 150 comprises a front surface 151, a rear surface 152, a right lateral surface 153 and a left lateral surface 154. The rear surface 152 is opposite the front surface 151 while the right lateral surface 153 is opposite the left lateral surface 154. Collectively, the surfaces 151-154 form the outer surface of the elongated handle body 150.

The elongated handle body 150 comprises an aperture 155 extending through the elongated handle body 150 from the top surface 151 to the bottom surface 152. The aperture 155 forms a laterally oriented passageway through the elongated handle body 150 and is provided to receive the grip body 170 (discussed in greater detail below). The aperture 155 preferably occupies more than one-half of the transverse cross-sectional area at point MP2. Nevertheless, other constructions are possible. The aperture 155 is located in the middle portion 116 of the handle 110.

The aperture 155 is defined by a sidewall 156 (FIG. 5) that tapers with increasing depth from both the front and rear surfaces 151, 152 of the elongated handle body 150, thereby coming to an annular apex/edge 157 (FIG. 5) that is located within the aperture 155 and is the narrowest part of the aperture 155. This dual-tapered sidewall geometry retains and allows dynamic positioning of the resilient grip body 170 during use of the toothbrush 100 and provides a weight shifting feature which improves control of the handle 110 during use.

The sidewall 156 of the aperture 155 extends beyond the front surface 151 and the rear surface 152 of the elongated handle body 150, thereby forming an annular ridge (or rim) 158 that protrudes from the front surface 151 of the elongated handle body 150 and an annular ridge (or rim) 159 that protrudes from the rear surface 152 of the elongated handle body 150. The annular ridges 158, 159 circumferentially surround the aperture 155 on both the front and rear surfaces 151, 152 of the elongated handle body 150.

The elongated handle body 150 further comprises a through slot 250 which is formed by an inner surface 251. The through slot 250 extends from the right lateral surface 153 to the left lateral surface 154 of the elongated handle body 150, thereby forming a laterally extending passageway through the elongated body 150. The through slot 250 is located in the proximal section 115 of the handle 110. Preferably, the through slot 250 is arranged at an approximately 90 degree offset from the aperture 155 (as measured circumferentially about the longitudinal axis A-A of the handle 110). The through slot 250 has a longitudinal cross-sectional area that occupies a majority of the longitudinal cross-sectional area of the proximal section 115 of the handle 110. Thought of another way, the through slot 250 occupies a majority of the volume of the proximal section 115 of the handle 110, preferably in a range of 55% to 95% and more preferably in a range of 75% to 90% of the volume of the proximal section 115 of the handle 110.

A plurality of internal projections, which are illustrated in the form of ridges 252, are provided that protrude from the inner surface 251 of the elongated handle body 150 and into the cavity of the through slot 250. Of course, the internal projections can take on other shapes, such as nubs, walls, mounds, etc.

The internal ridges 252 are preferably arcuate in shape and extend laterally across the substantial entirety of the width of the inner surface 251 in a spaced-apart manner. The arcuate internal ridges 252 are arranged in pairs wherein the two arcuate internal ridges 252 which make up each pair are oriented so that their concave sides oppose one another, thereby collectively forming a segmented circular internal ridge. The internal ridges 252 are sized and shaped to correspond to the grooves 248 of the core structure 140. As will be discussed in greater detail below, when the toothbrush 100 is assembled and the core structure 140 is disposed within the through slot 250 of the elongated handle body 150, the ridges 252 of the elongated handle body 150 extend into and fill the grooves 248 of the core structure 140. The cooperation of the ridges 252 and the grooves 248 helps mechanically secure the core structure 140 within the through slot 250 so that the core structure 140 does not become dislodged from the elongated handle body 150 during repeated use of the toothbrush 100.

A pair of longitudinally extending linear ridges 253 also protrude from the inner surface 251 into the cavity of the through slot 250. The arcuate ridges 252 are located between the linear ridges 253. These linear ridges 253 extend into and fill the linear grooves 249 of the core structure 140 when the core structure 140 is disposed within the through slot 250.

A longitudinally extending channel 254 (which can also be referred to as a groove or depression) is provided in the outer surface of the elongated handle body 150. The channel 254 is a U-shaped channel that starts on the front surface 151 of the elongated handle body 150, wraps around a proximal end 255 of the elongated handle body 150, and continues onto the rear surface 152 of the elongated handle body 150. More specifically, the channel 254 extends longitudinally from the transition point TP2 on the front surface 151 to the proximal end 255, wraps around the proximal end 255, and extends longitudinally from the proximal end 255 back to the transition point TP2 on the rear surface 152. The channel 254 thereby extends along both the proximal section 115 and middle section 116 of the handle 110. The channel 254 surrounds the aperture 155 on both the front and rear surfaces 151, 152 (specifically the annular ridges 158, 159). As will be described in greater detail below, the channel 254 receives and is filled with the grip cover 160.

A plurality of through holes 256 are provided in the elongated handle body 150 that form passageways into the through slot 250 from the front and rear surfaces 151, 152. In the illustrated embodiment, two through holes 256 are provided on each of the front and rear surfaces 151, 152 of the elongated handle body 150 within the channel 254. The through holes 256 on the front surface 151 are generally aligned with the through holes 256 on the rear surface 152. A first pair of the through holes 256 are located adjacent the proximal end 255 of the elongated handle body 150 while a second pair of the through holes 256 are located adjacent the transition point TP1. Of course, more or less of the through holes 256 can be provided as needed and their location can be varied. As described in greater detail below, the through holes 256 are the result of the tooling used to support the core structure 140 during the injection overmolding of the elongated handle body 150 about the core structure 140. However, the through holes 256 also receive the protuberances 240-243 of the core structure to provide a mechanical connection between the core structure 140 and the elongated handle body 150 when the core structure 140 is disposed within the elongated handle body 150.

At least one outer projection 257 (best visible in FIGS. 3 and 5) is provided on the rear surface 152 of the elongated handle body 150. Preferably, a plurality of spaced apart outer projections 257 are provided that protrude from the rear surface 152. While the outer projections 257 could have virtually any shape, they are preferably in the form of spaced-apart arcuate ridges (or ribs) that laterally extend the width of the rear surface 152. In the preferred embodiment, the outer arcuate ridges 257 correspond to the arcuate internal ridges 252 in shape and positioning on the elongated handle body 150. The arcuate outer ridges 257 are arranged in pairs wherein the two arcuate outer ridges 257 which make up each pair are oriented so that their concave sides oppose one another, thereby collectively forming a segmented circular internal ridge.

The arcuate outer ridges 257 preferably span laterally between the lateral surfaces 113, 114 of the handle 110, although they may have different transverse lengths. The transverse length of each arcuate outer ridge 257 generally matches the width at the longitudinal location along the handle 110. However, the arcuate outer ridges 257 are preferably slightly short of the actual width of handle 110 at any one location so as to be covered on the sides by grip cover 160. Since arcuate outer ridges 257 span the width of the handle 110 in the proximal and middle sections 115, 116, they each have varying lengths due to the variations in the width of these sections 115, 116.

As a result of the spaced-apart arrangement of the arcuate outer ridges 257, a transverse channel or groove is defined between each of the adjacent arcuate outer ridges 257. These transverse channels are configured to receive and retain the material of the grip cover 160, such as a thermoplastic elastomer (TPE) or other similar materials used in oral care products.

The elongated handle body 150 is preferably a unitary single component constructed of a rigid material, such as for example a hard plastic. Suitable hard plastics include polyethylene, polypropylene (PP), polyamide, polyester, cellulosics, SAN, acrylic, ABS or any other of the commonly known thermoplastics used in toothbrush manufacture. Preferably, the elongated handle body 150 is constructed of a hard plastic material that is a different type of plastic than the hard plastic material of which the core structure 140 is constructed. Most preferably, the elongated handle body is constructed of an opaque PP.

The grip cover 160 is a generally U-shaped (or tong-shaped) cover or layer of resilient material. The grip cover 160 is fixed to the elongated base handle 150 to provide a gripping surface to improve performance during use. The grip cover 160 is positioned within the channel 254 of the elongated handle base 150 when the toothbrush 100 is in an assembled state.

The grip cover 160 conceptually comprises three sections, a front leg 161, a rear leg 162 and a curved segment 165 that connects the front and rear legs 161, 162 in an opposing manner. The overall shape and size of the front and rear legs 161, 162 are mirror images of one another and, thus, are equal in length, width and overall shape and size. A first opening 167 is provided in the front leg 161 while a second opening 168 is provided in the rear leg 162. The first and second openings 167, 168 receive the annular ridges/rims 158, 159 of the elongated handle body 150 when the grip cover 160 is fixed to the elongated handle body 150.

The rear leg 162 comprises a plurality of spaced-apart openings 166, preferably in the form of arcuate slots that extend transversely across the rear leg 162. The openings 166 are sized, shaped and positioned to be aligned with the outer arcuate ridges 257 of the elongate handle body 150. When the grip cover 160 is fixed to the elongate handle body 150, the outer arcuate ridges 257 extend into the openings 166 and are thus exposed via the openings 166. To form openings 166, suitable injection molding equipment mates with the top surfaces of the outer arcuate ridges 257 to prevent overmolding of the outer arcuate ridges 257 and any undesired deflection of the elongated handle base 150 during the molding process. This enables the top surfaces of the outer arcuate ridges 257 to be exposed after the molding process that adds the grip cover 160 to the base 150.

Figure 5:
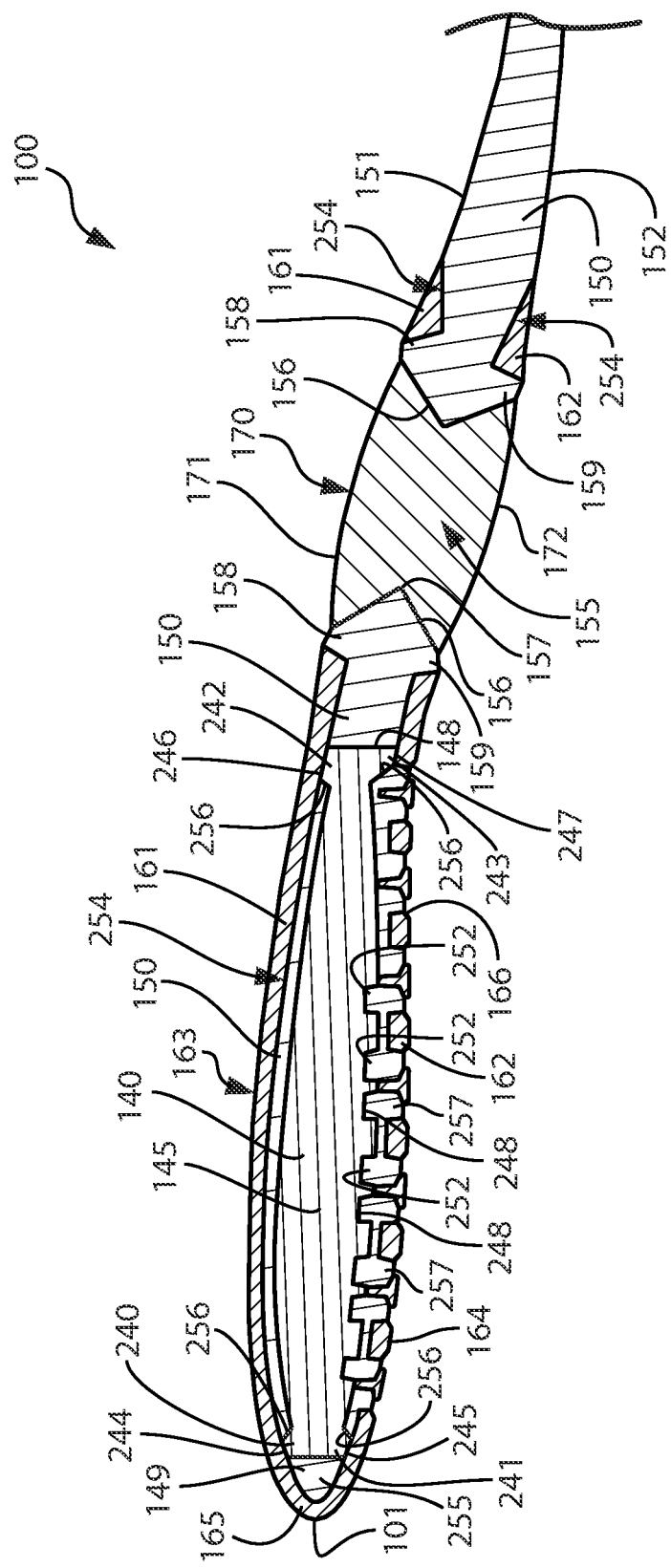
FIG. 5 is a longitudinal cross-sectional view of the toothbrush of FIG. 1 taken along view V-V of FIG. 2 according to one embodiment of the present invention.

As can be seen best in FIG. 5, the top surfaces of the outer arcuate ridges 257 are preferably recessed in the openings 166 relative to the outer surface 164 of the rear leg 162 of the grip cover 160. In other words, the grip cover 160 is created to have a sufficient thickness so as to control the depth of the openings 166. By ensuring that the top surfaces of the outer arcuate ridges 257 are depressed relative to the outer surface 164 of the rear leg 162 of the grip cover 160, the openings 166 prevent slippage of the handle 110 by enabling portions of the user's fingers to slightly protrude into the depth of the openings 166. Additionally, openings 166 channel water away from the fingers tips during wet operational conditions. Air is also able to enter the openings during brushing to provide some evaporative effect.

The grip cover 160 is preferably constructed of a resilient material, such as a thermoplastic elastomer (TPE). To provide comfort as well as control benefits, the elastomeric material of the grip cover 160 preferably has a hardness durometer measurement in the range of A13 to A50 Shore hardness, although materials outside this range may be used. A more preferred range of the hardness durometer rating is A25 to A40 Shore hardness. Furthermore, while an injection molded construction of the grip cover 160 is preferred, the grip cover 160 may, in some embodiments, be formed as a thin layer and attached to elongated handle base 150 with an appropriate adhesive, sonic welding, thermal welding or other technique.

The grip body 170 is a generally bulbous shaped body that bulges out of the aperture 155 of the elongated handle body 150. The grip body 170 fills the aperture 155 of the elongated handle body 150 and, thus, takes on the shape of the aperture 155. The grip body has a convex front surface 171 and a convex rear surface 172, which resemble an oval or elliptical shape. The bulbous shape of the grip body 170 enables the user to reliably roll and control the handle 110 between the thumb and index fingers during use. The grip body 170 may also be non-bulging or have any number of shapes, such as circular, a true oval shape and the like.

In one preferred construction, the grip body 170 has a multiplicity of finger grip protrusions 173 projecting from the front and rear surfaces 171, 172. The finger grip protrusions 173 provide a tactile feature to increase the friction on the user's finger surfaces and thus enhance the user's ability to grip the handle 110, particularly under wet conditions. The finger grip protrusions 173 are preferably provided in a desired conical or frusto-conical shape for improved grip performance. Of course, other roughened surfaces could be used.

The grip body 170 is constructed of a resilient material, such as a soft thermoplastic elastomer (TPE). To provide optimum comfort as well as control benefits, the resilient materials of the grip body 170 preferably has a hardness durometer in a range of A11 to A15 Shore hardness. Of course, materials outside this hardness range could also be used. As an example, one preferred elastomeric material for the grip body 170 is styrene-ethylene/butylene-styrene (SEBS) manufactured by GLS Corporation. Nevertheless, other manufacturers can supply the SEBS material and other materials could be used.

Preferably, the grip body 170 is constructed of a different type of resilient material than that which the grip cover 160 is constructed. For example, it is preferred that the grip body 170 be constructed of a resilient material having a different hardness as compared to the hardness of the grip cover 160. The material of the grip body 170 is preferably softer than the material forming the grip cover 160. In this manner, the handle 110 may be provided with different grip features to complement the particular control need. The material of the resilient grip body 170 and the grip cover 160 are preferably each a thermoplastic elastomer.

Figure 6:
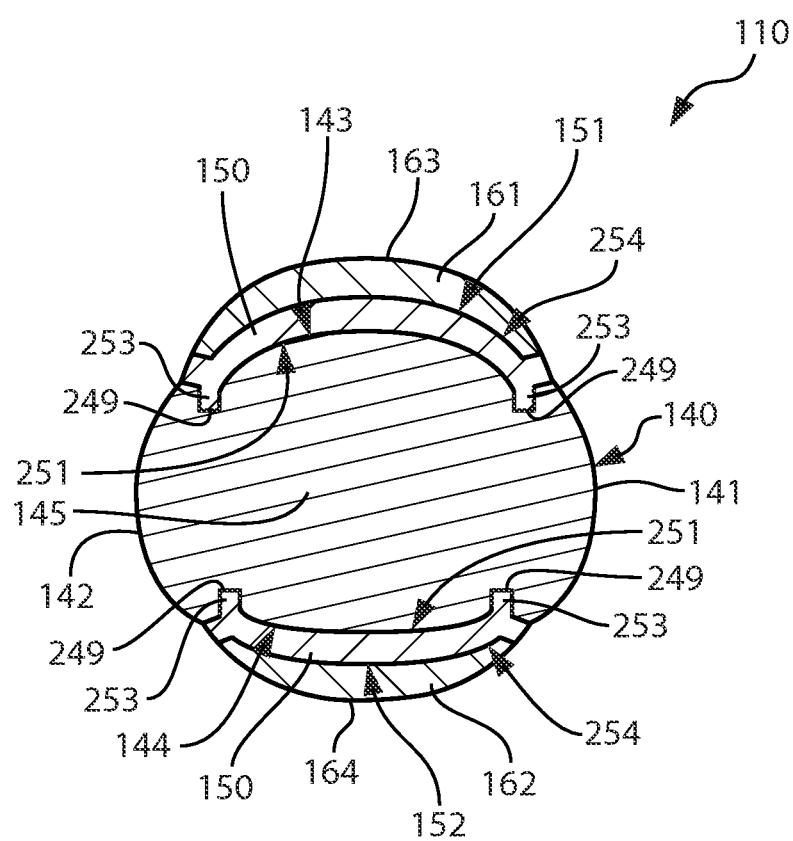
FIG. 6 is a lateral cross-sectional view of the toothbrush of FIG. 1 taken along view VI-VI of FIG. 3 according to one embodiment of the present invention.

Referring now to FIGS. 1, 5 and 6 concurrently, the structural cooperation of the four components 140, 150, 160, 170 of the toothbrush 100 will now be described in detail with respect to a preferred construction. In the preferred construction, the elongated handle body 150 is constructed of opaque PP, the core structure 140 is constructed of transparent SAN, the grip body 170 is constructed of a TPE having a first hardness, and the grip cover 160 is constructed of a TPE having a second hardness that is greater than the first hardness.

The core structure 140 is disposed within and fills the through slot 250 of the elongated handle body 150. As a result, the core structure 140 is partially surrounded by the elongated handle body 150 in a circumferential manner. More specifically, the core structure 140 is within the through slot 250 so that the elongated handle body 150 overlies (and thus covers) only the front and rear surfaces 143, 144 of the core structure 140. The right and left lateral surfaces 141, 142 of the core structure 140 protrude from the through slot 250 and remain exposed on the handle 110 so that a user can view into and/or through the core structure 140. In essence, the core structure 140 provides a window into and through the handle 110.

The core structure 140 is located within the through slot 250 so that the protuberances 240-243 of the core structure 140 extend into the through holes 256 of the elongated handle body 150. As a result, the contact surfaces 244-247 of the core structure 140 are exposed in the through holes 256 of the elongated handle body 150. The extension of the protuberances 240-243 into the through holes 256 provides a mechanical connection between the core structure 140 and the elongated handle body 150 that assists in preventing unwanted relative rotation and/or separation of the core structure 140 from the elongated handle body 150 during repeated use. Such a mechanical connection is desirable as the SAN of the core structure 140 and the PP of the elongated handle body 150 do not form a chemical bond with each other during the injection molding process.

Additionally, the inner arcuate ridges 252 of the elongated handle body 150 extend into and nest within the arcuate grooves 248 of the core structure 140, thereby increasing the mechanical fitting connection between the core structure 140 and the elongated handle body 150.

The grip body 170 is disposed within and fills the aperture 155 of the elongate handle body 150. The convex front and rear surfaces 171, 172 of the grip body 170 bulge from the aperture 155 and form a portion of the front and rear surfaces 111, 112 of the overall handle 110. The grip body 170 is preferably formed in the aperture 155 via a one or two shot injection molding technique. The tapered shape of the sidewalls 156 of the aperture help retain the grip body 170 within the aperture over the life cycle of the toothbrush 100. Additionally, a chemical bond may be formed between the TPE of the grip body 170 and the PP of the elongated handle body 150 during the injection molding process.

The grip cover 160 is applied to the outer surface of the elongated handle body 150 once the core structure 140 is properly located within the through slot 250 as discussed above. More specifically, the grip cover 160 is fixed to the elongated handle body 150 so that: (1) the front leg 161 of the grip cover 160 nests within the portion of the channel 254 on the front surface 151 of the elongated handle body 150; (2) the curved portion 165 of the grip cover 160 nests within the portion of the channel 254 that wraps around the proximal end 255 of the elongated handle body 150; and (3) the rear leg 162 of the grip cover 160 nests within the portion of the channel 254 on the rear surface 152 of the elongated handle body 150. As a result, the grip cover 160 overlies and conceals the through holes 256 of the elongated handle body 150. More specifically, the front leg 261 overlies and conceals the through holes 256 on the front surface 151 of the elongated handle body 150 while the rear leg 262 overlies and conceals the through holes 256 on the rear surface 152 of the elongated handle body 150.

The outer arcuate ridges 257 of the elongated handle body 150 extend into the openings 166 of the grip cover 160 but remain depressed below the rear surface 164 of the rear leg 162 of the grip cover 160 as discussed above. The grip cover 160 fills the channel 254, thereby wrapping around the proximal end 155 of the elongated handle body 150 and surrounding the aperture 155 on both the front and rear surfaces 151, 152 of the elongated handle body 150. The grip cover 160 also fills the transverse channels/slots between the outer arcuate ridges 257 of the elongated handle body 150.

The grip body 160 is fixed to the elongated handle body 150 by a chemical bond that is formed between the TPE of the grip cover 160 and the PP of the elongated handle body 150 during the injection molding process. Finally, while grip cover 160 is shown as a single unitary member or layer, it could be formed by separate independent parts or sections in certain embodiments.

Figure 8:
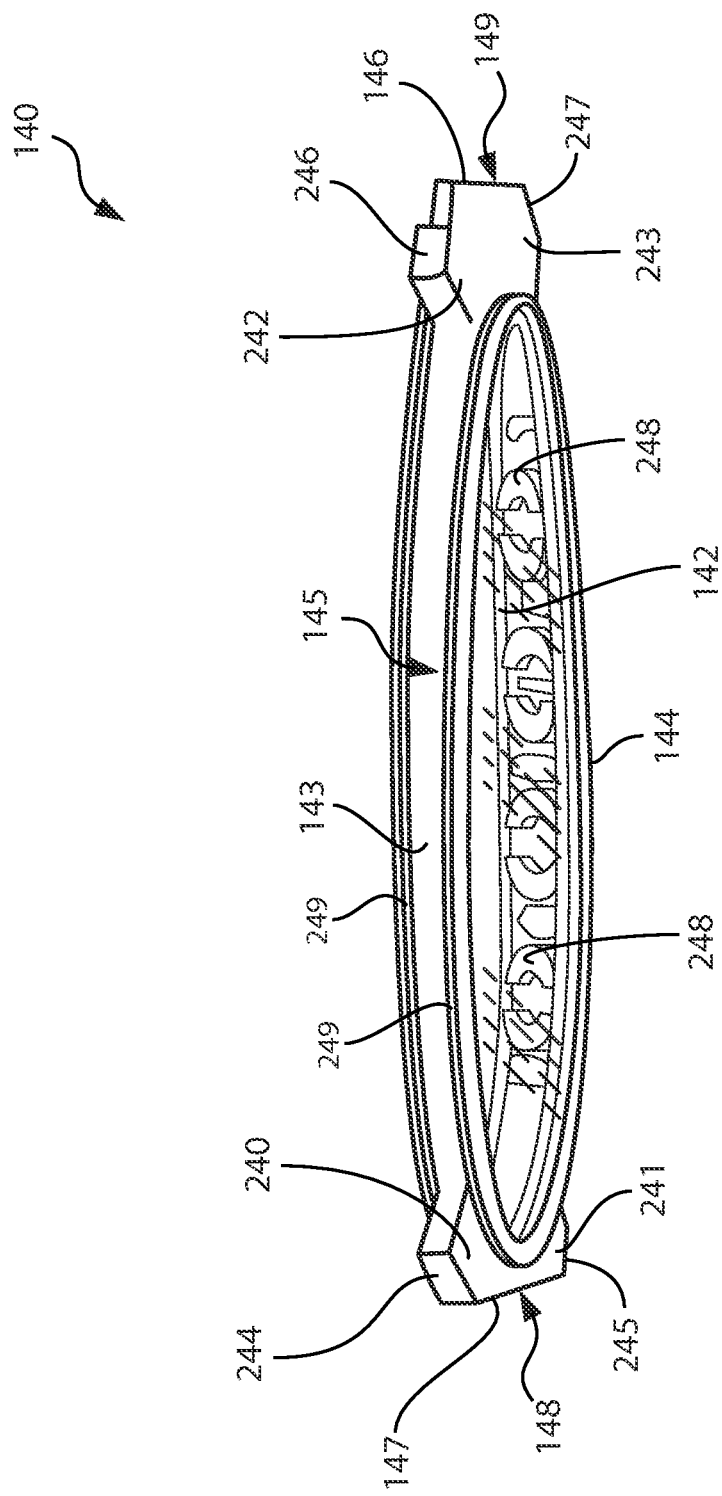
FIG. 8 is a perspective view of a core structure of the handle of the toothbrush of FIG. 1 according to one embodiment of the present invention.
Figure 9:
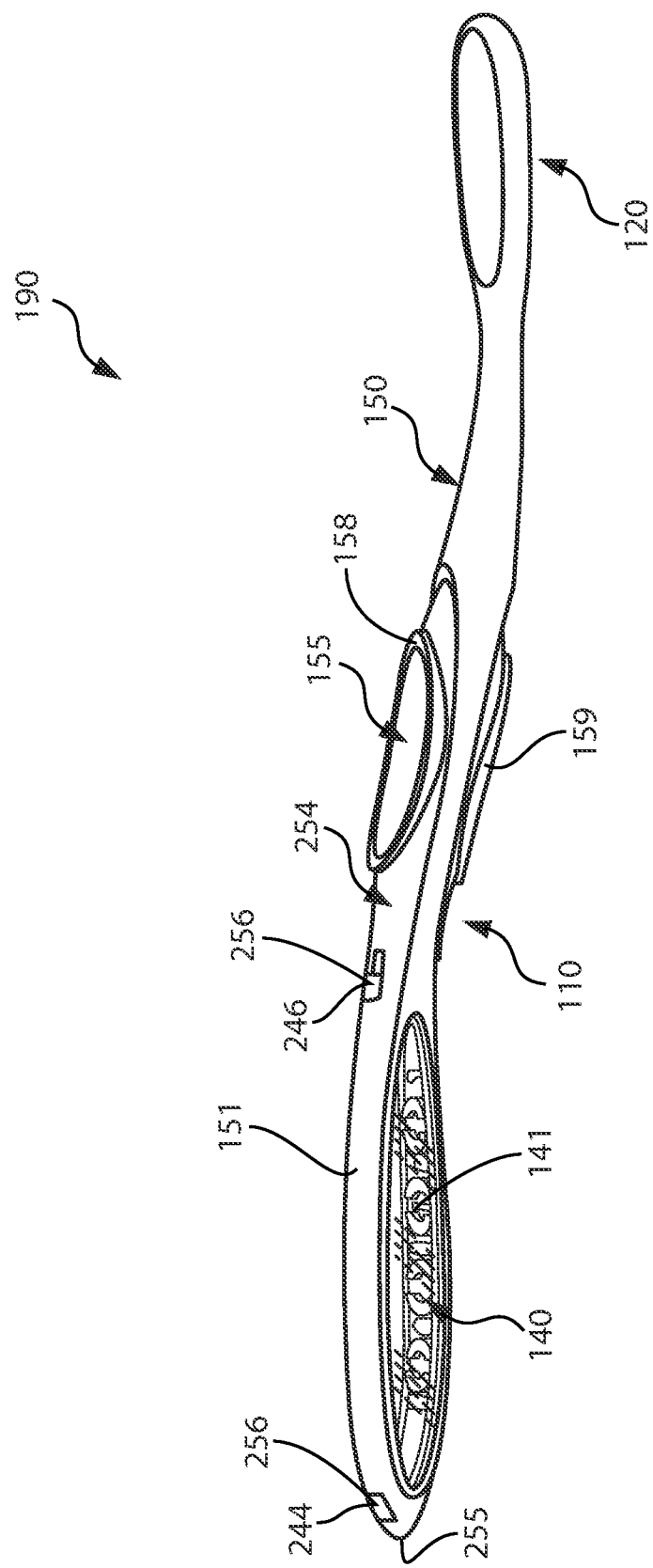
FIG. 9 is a perspective view of a handle assembly consisting of the core structure of FIG. 8 with the elongated handle body overmolded thereto according to one embodiment of the present invention.
Figure 10:
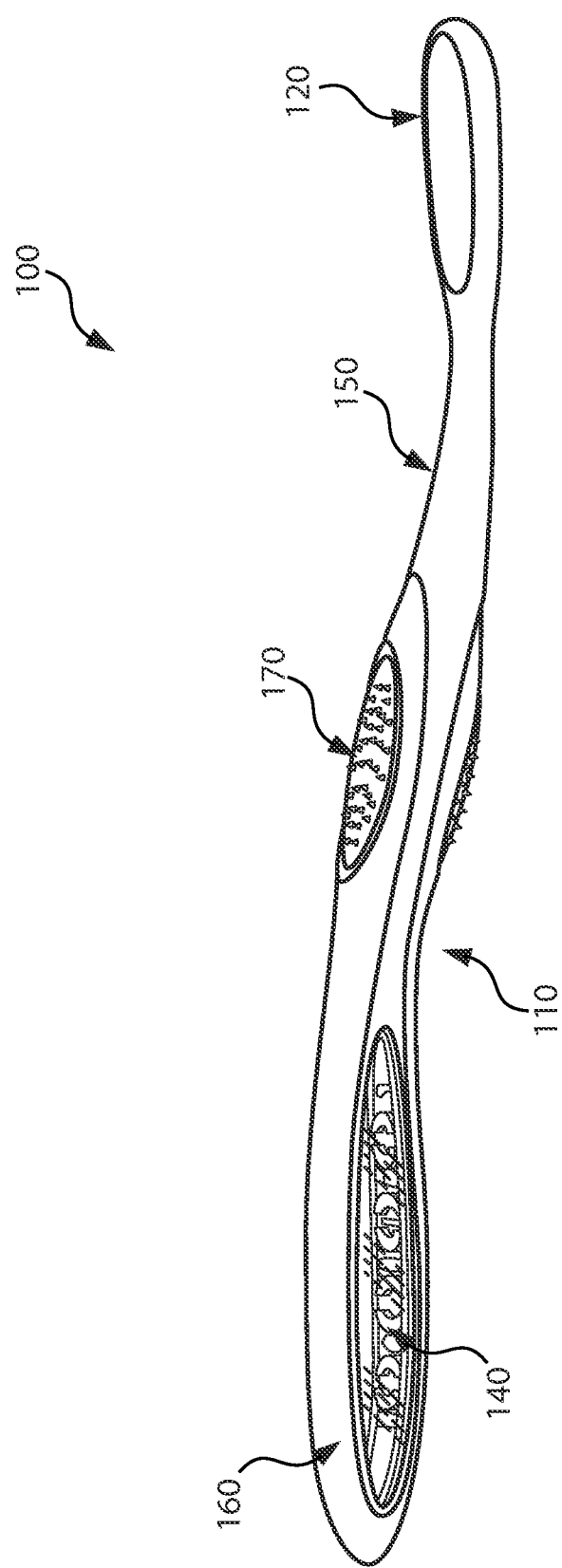
FIG. 10 is a perspective view of the handle consisting of the handle assembly of FIG. 9 with the grip cover overmolded to the elongated handle body according to one embodiment of the present invention.

Referring now to FIGS. 8-10, a method of manufacturing the toothbrush 100 according to one embodiment of the present invention will be described.

The first component created in manufacturing the toothbrush 100 is the core structure 140. To create the core structure 140, a first mold is provided having a first mold cavity and at least one port/nozzle for injecting liquefied SAN into the first mold cavity. Preferably a single port is used to inject the liquefied SAN. The first mold cavity has a volume that is sized and shaped to correspond to the core structure 140. The first mold may be two-part mold, as is known in the art. Once the first mold cavity is created/provided, liquefied SAN is injected into the first mold so as to fill the first mold cavity. The liquefied SAN is allowed to cool to an appropriate temperature so as to form the core structure 140, as shown in FIG. 8, for further handling.

Once the core structure 140 is created (and allowed to adequately cool for further handling), the core structure 140 is supported by one or more clamping members that engage one or more points of contact on the contact surfaces 244-247 with at least one set of arms.

Once the clamping member is properly supporting the core structure 140 through surface contact created between its arms and the contact surfaces 244-247, the core structure 140 is positioned within a second mold cavity of a second mold. This positioning can be effectuated by either moving the core structure 140 into the second mold cavity or by creating the second mold cavity about the core structure 140 while supporting the core structure 140 in a stationary manner, which can be accomplished by translating and mating multiple pieces of the second mold into position so that the second mold cavity is formed about the core structure 140. The second mold cavity has a volume that is sized and shaped to correspond to the handle assembly 190 (FIG. 9). One or more ports are present in the second mold for injecting liquefied PP into the second mold cavity. Preferably a single port is used to inject the liquefied PP.

Once the core structure 140 is in proper position within the second mold cavity (and the second mold cavity is adequately sealed), the liquefied PP is injected into the second mold cavity so as to fill the remaining volume of the second mold cavity that is not occupied by the core structure 140. The liquefied PP partially surrounds the core structure 140, which remains supported by the clamping member (as described above) during the injection and filling of the second mold cavity with the liquefied PP.

The liquefied PP is then allowed to cool to an appropriate temperature, thereby forming the elongated handle body 150 about the core structure 140, as shown in FIG. 9. The core structure 140 and elongated handle body 150 collectively form a handle assembly 190 (illustrated in FIG. 9). As a result of the core structure 140 being supported at the contact surfaces 244-247 by the arms of the clamping member during the formation of the elongated handle body 150, the liquefied PP surrounds the arms of the clamping (and does not cover the contact surfaces 244-247). Thus, upon cooling of the liquefied PP (i.e., the formation of the elongated handle body 150), the removal of the arms of the clamping member from the core structure 140 results in through holes 256 being formed in the front and rear surfaces 151, 152 of the elongated handle body 150 through which the contact surfaces 244-247 are exposed. The SAN material of the core structure 140 does not chemically bond with the PP of the elongated handle body 150 during the injection molding process.

Once the handle assembly 190 is sufficiently cool for further handling, the handle portion 110 is positioned within a third mold cavity of a third mold. The handle assembly 190 is preferably supported by the head 120 during this process. The third mold cavity has a volume that is sized and shaped to receive the handle portion 110 of the handle assembly 190 while leaving a remaining volume open that corresponds to the grip cover 160. One or more ports are present in the third mold for injecting liquefied TPE into the remaining volume of the third mold cavity. Preferably a single port is used to inject the liquefied TPE of the grip cover 160.

Once the handle portion 110 of the handle assembly 190 is in proper position within the third mold cavity, the liquefied TPE is injected into the third mold cavity so as to fill the remaining volume of the third mold cavity that is not occupied by the handle portion 110 of the handle assembly 190. As a result, the liquefied TPE fills the channel 254 of the elongated handle body 150 thereby forming an overmolded grip cover 160 that is fixed to the elongated handle body 150. The TPE of the grip cover 160 is then allowed to cool. The TPE material of the grip cover 160 chemically bonds with the PP of the elongated handle body 150 during this injection molding process.

Either before, after or simultaneously with forming the grip cover 160, the aperture 155 of the elongated handle body 150 is filled with a soft TPE to form the grip body 170. This is achieved by injecting the liquefied soft TPE into the aperture 155, which is enclosed by an appropriate mold, via a port that is in fluid communication with the aperture 155. The mold can be a fourth mold or it can be the third mold. In instances where the third mold is used, the third mold would include a fourth mold cavity that is isolated from the third mold cavity. The TPE material of the grip body 170 chemically bonds with the PP of the elongated handle body 150 during this injection molding process.

The inventive aspects discussed above may be practiced for a manual toothbrush or a powered toothbrush. In operation, the previously described features, individually and/or in any combination, improve the control, grip performance, aesthetics and cost point of oral implements. Other constructions of toothbrush are possible. For example, the head 120 may be replaceable or interchangeable on the handle 110. The head 120 may include various oral surface engaging elements, such as inter-proximal picks, brushes, flossing element, plaque scrapper, tongue cleansers and soft tissue massages. While the various features of the toothbrush 100 work together to achieve the advantages previously described, it is recognized that individual features and sub-combinations of these features can be used to obtain some of the aforementioned advantages without the necessity to adopt all of these features in an oral care implement.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement comprising:
   a handle having a proximal end and a distal end;
   a head connected to the distal end of the handle;
   the handle comprising a core structure comprising a first rigid material, an elongated handle body comprising a second rigid material, and a grip cover comprising a resilient material;
   wherein the elongated handle body comprises the head; and
   wherein the core structure is disposed in a through slot that extends from opposite surfaces of the elongated handle body, and wherein surfaces of the core structure remain exposed via the through slot.

2. The oral care implement of claim 1 wherein the grip cover is shaped and covers a portion of a front surface of the elongated handle body, a proximal end of the elongated handle body and a portion of a rear surface of the elongated handle body.

3. The oral care implement of claim 1 wherein the grip cover is located within a channel formed into the elongated handle body.

4. The oral care implement of claim 1 wherein the first rigid material is a first hard plastic and the second rigid material is a second hard plastic.

5. The oral care implement of claim 4 wherein the first and second hard plastics are chemically incompatible with each other so as to not form a chemical bond with each other during an injection molding process.

6. The oral care implement of claim 5 wherein the first hard plastic is SAN and the second hard plastic is PP.

7. The oral care implement of claim 5 wherein the resilient material is chemically compatible with the second hard plastic so as to form a chemical bond with the second hard plastic during an injection molding process.

8. The oral care implement of claim 1 wherein the elongated handle body comprises a from surface, a rear surface, a right lateral surface, and a left lateral surface, and wherein the through slot extends from the right lateral surface of the elongated handle body to the left lateral surface of the elongated handle body thereby forming a laterally extending passageway through the elongated body.

9. The oral care implement of claim 8 wherein the core structure is exposed at the right and left lateral surfaces of the elongated handle body.

10. The oral care implement of claim 9 wherein the core structure has a right lateral surface and a left lateral surface, and wherein an overall right lateral surface of the handle is formed collectively by the right lateral surface of the elongated handle body and the right lateral surface of the core structure and wherein an overall left lateral surface of the handle is formed collectively by the left lateral surface of the elongated handle body and the left lateral surface of the core structure.

11. The oral care implement of claim 10 further comprising an aperture extending through the elongated handle body from the front surface of the elongated handle body to the rear surface of the elongated handle body.

12. The oral care implement of claim 11 further comprising a grip body constructed of a resilient material filling the aperture so that a front surface and a rear surface of the grip body are exposed on the handle.

13. The oral care implement of claim 12 wherein the grip cover is U-shaped and covers a portion of the front surface of the elongated handle body, a proximal end of the elongated handle body and a portion of the rear surface of the elongated handle body.

14. The oral care implement of claim 13 wherein the core structure is transparent and has a front surface and an opposing rear surface, and wherein the rear surface of the core structure comprises a plurality of arcuate grooves that form depressions in the rear surface of the core structure.

15. The oral care implement of claim 14 wherein the arcuate grooves are arranged in pairs in a spaced apart manner, concave sides of the arcuate grooves of each pair facing one another.

16. The oral care implement of claim 15 wherein the core structure is constructed of a transparent hard plastic so that the arcuate grooves on the rear surface of the core structure are visible through the right and left lateral surfaces of the core structure.

17. The oral care implement of claim 16 further comprising a first through hole formed into the front surface of the elongated handle body that forms a first passageway into the through slot and a second through hole formed into the rear surface of the elongated handle body that forms a second passageway into the through slot.

18. The oral care implement of claim 17 wherein the core structure comprises a first protuberance that extends into the first through hole on the front surface of the elongated handle body and a second protuberance that extends into the second through hole on the rear surface of the elongated handle body.

19. The oral care implement of claim 18 further comprising a third through hole formed into the front surface of the elongated handle body that forms a third passageway into the through slot, the core structure comprising a third protuberance that extends into the third through hole on the front surface of the elongated handle body.

20. The oral care implement of claim 19 wherein the grip cover covers the first, second and third protuberances of the core structure.

* * * * *